US008568488B2

(12) United States Patent
Stack et al.

(10) Patent No.: US 8,568,488 B2
(45) Date of Patent: *Oct. 29, 2013

(54) SATIATION DEVICES AND METHODS

(75) Inventors: Richard S. Stack, Chapel Hill, NC (US); Richard A. Glenn, Chapel Hill, NC (US); William L. Athas, Durham, NC (US); Michael S. William, Santa Rosa, CA (US); Trevor J. Moody, Seattle, WA (US); Fred E. Silverstein, Seattle, WA (US); Nathan Every, Seattle, WA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 62 days.

This patent is subject to a terminal disclaimer.

(21) Appl. No.: 12/572,153

(22) Filed: Oct. 1, 2009

(65) Prior Publication Data
US 2010/0016988 A1 Jan. 21, 2010

Related U.S. Application Data

(63) Continuation of application No. 10/345,914, filed on Jan. 16, 2003, now abandoned, which is a continuation-in-part of application No. 09/940,110, filed on Aug. 27, 2001, now Pat. No. 6,675,809, and a continuation-in-part of application No. 10/118,289, filed on Apr. 8, 2002, now Pat. No. 6,845,776.

(60) Provisional application No. 60/379,306, filed on May 10, 2002.

(51) Int. Cl.
A61F 2/04 (2013.01)
A61M 5/00 (2006.01)

(52) U.S. Cl.
USPC ............... 623/23.7; 623/23.65; 604/7; 604/8

(58) Field of Classification Search
None
See application file for complete search history.

(56) References Cited

U.S. PATENT DOCUMENTS 1,408,865 A 3/1922 Cowell
3,663,965 A 5/1972 Lee et al.
(Continued)

FOREIGN PATENT DOCUMENTS

CH 680263 A5 7/1992
EP 0 775 471 B1 5/1997
(Continued)

OTHER PUBLICATIONS

International Search Report from PCT Patent Application No. PCT/US2002/027177 mailed Feb. 14, 2003.
International Search Report from PCT Patent Application No. PCT/US2003/004378 mailed Aug. 13, 2003.
International Search Report from PCT Patent Application No. PCT/US2003/033605 mailed Mar. 29, 2004.
International Search Report from PCT Patent Application No. PCT/US2003/033606 mailed Mar. 29, 2004.
(Continued)

*Primary Examiner* — David Isabella
*Assistant Examiner* — Javier Blanco
(74) *Attorney, Agent, or Firm* — Bookoff McAndrews, PLLC

(57) ABSTRACT

A satiation device is described which includes a sheath or liner extending from the proximal or middle stomach to the distal antrum. Food ingested by the patient passes through the sheath or liner, thereby minimizing contact between the ingested food and the stomach. It is believed that over time, reduced contact between food and the stomach will result in decreased Ghrelin production by the patient and a consequent decrease in appetite. In some embodiments, the satiation device may also include a proximal pouch and/or a distal bypass tube.

2 Claims, 10 Drawing Sheets

(56) References Cited

U.S. PATENT DOCUMENTS

| | | |
|---|---|---|
| 4,134,405 A | 1/1979 | Smit |
| 4,207,890 A | 6/1980 | Mamajek et al. |
| 4,246,893 A | 1/1981 | Berson |
| 4,315,509 A | 2/1982 | Smit |
| 4,331,277 A | 5/1982 | Green |
| 4,403,604 A | 9/1983 | Wilkinson et al. |
| 4,416,267 A | 11/1983 | Garren et al. |
| 4,417,360 A | 11/1983 | Moasser |
| 4,441,215 A | 4/1984 | Kaster |
| 4,467,804 A | 8/1984 | Hardy et al. |
| 4,485,805 A | 12/1984 | Foster, Jr. |
| 4,501,264 A | 2/1985 | Rockey |
| 4,607,618 A | 8/1986 | Angelchik |
| 4,641,653 A | 2/1987 | Rockey |
| 4,648,383 A | 3/1987 | Angelchik |
| 4,694,827 A | 9/1987 | Weiner et al. |
| 4,723,547 A | 2/1988 | Kullas et al. |
| 4,747,849 A | 5/1988 | Galtier |
| 4,846,836 A | 7/1989 | Reich |
| 4,848,367 A | 7/1989 | Avant et al. |
| 4,899,747 A | 2/1990 | Garren et al. |
| 4,925,446 A | 5/1990 | Garay et al. |
| 4,946,440 A | 8/1990 | Hall |
| 4,969,896 A | 11/1990 | Shors |
| 4,997,084 A | 3/1991 | Opie et al. |
| 5,006,106 A | 4/1991 | Angelchik |
| 5,037,021 A | 8/1991 | Mills et al. |
| 5,061,275 A | 10/1991 | Wallsten et al. |
| 5,084,061 A | 1/1992 | Gau et al. |
| 5,088,979 A | 2/1992 | Filipi et al. |
| 5,163,952 A | 11/1992 | Froix |
| 5,211,658 A | 5/1993 | Clouse |
| 5,234,454 A | 8/1993 | Bangs |
| 5,246,456 A | 9/1993 | Wilkinson |
| 5,259,399 A | 11/1993 | Brown |
| 5,263,629 A | 11/1993 | Trumbull et al. |
| 5,290,217 A | 3/1994 | Campos |
| 5,306,300 A | 4/1994 | Berry |
| 5,314,473 A | 5/1994 | Godin |
| 5,327,914 A | 7/1994 | Shlain |
| 5,345,949 A | 9/1994 | Shlain |
| 5,355,897 A | 10/1994 | Pietrafitta et al. |
| 5,401,241 A | 3/1995 | Delany |
| 5,403,326 A | 4/1995 | Harrison et al. |
| 5,405,377 A | 4/1995 | Cragg |
| 5,431,673 A | 7/1995 | Summers et al. |
| 5,486,187 A | 1/1996 | Schenck |
| 5,514,176 A | 5/1996 | Bosley, Jr. |
| 5,535,935 A | 7/1996 | Vidal et al. |
| 5,542,949 A | 8/1996 | Yoon |
| 5,562,239 A | 10/1996 | Boiarski et al. |
| 5,571,116 A | 11/1996 | Bolanos et al. |
| 5,577,654 A | 11/1996 | Bishop |
| 5,593,434 A | 1/1997 | Williams |
| 5,597,107 A | 1/1997 | Knodel et al. |
| 5,609,624 A | 3/1997 | Kalis |
| 5,628,786 A | 5/1997 | Banas et al. |
| 5,630,539 A | 5/1997 | Plyley et al. |
| 5,647,526 A | 7/1997 | Green et al. |
| 5,653,743 A | 8/1997 | Martin |
| 5,662,713 A | 9/1997 | Andersen et al. |
| 5,673,841 A | 10/1997 | Schulze et al. |
| 5,674,241 A | 10/1997 | Bley et al. |
| 5,706,998 A | 1/1998 | Plyley et al. |
| 5,709,657 A | 1/1998 | Zimmon |
| 5,720,776 A | 2/1998 | Chuter et al. |
| 5,749,918 A | 5/1998 | Hogendijk et al. |
| 5,762,255 A | 6/1998 | Chrisman et al. |
| 5,771,903 A | 6/1998 | Jakobsson |
| 5,785,684 A | 7/1998 | Zimmon |
| 5,792,119 A | 8/1998 | Marx |
| 5,820,584 A | 10/1998 | Crabb |
| 5,839,639 A | 11/1998 | Sauer et al. |
| 5,848,964 A | 12/1998 | Samuels |
| 5,855,311 A | 1/1999 | Hamblin et al. |
| 5,855,601 A | 1/1999 | Bessler et al. |
| 5,856,445 A | 1/1999 | Korsmeyer |
| 5,861,036 A | 1/1999 | Godin |
| 5,868,141 A | 2/1999 | Ellias |
| 5,887,594 A | 3/1999 | LoCicero, III |
| 5,897,562 A | 4/1999 | Bolanos et al. |
| 5,910,144 A | 6/1999 | Hayashi et al. |
| 5,922,019 A | 7/1999 | Hankh et al. |
| 5,947,983 A | 9/1999 | Solar et al. |
| 5,993,473 A | 11/1999 | Chan et al. |
| 5,993,483 A | 11/1999 | Gianotti |
| 6,016,848 A | 1/2000 | Egres, Jr. |
| 6,051,015 A | 4/2000 | Maahs |
| 6,086,600 A | 7/2000 | Kortenbach |
| 6,098,629 A | 8/2000 | Johnson et al. |
| 6,102,922 A | 8/2000 | Jakobsson et al. |
| 6,113,609 A | 9/2000 | Adams |
| 6,120,534 A | 9/2000 | Ruiz |
| 6,146,416 A | 11/2000 | Andersen et al. |
| 6,159,146 A | 12/2000 | El Gazayerli |
| 6,159,238 A | 12/2000 | Killion et al. |
| 6,197,022 B1 | 3/2001 | Baker |
| 6,206,930 B1 | 3/2001 | Burg et al. |
| 6,245,088 B1 | 6/2001 | Lowery |
| 6,251,132 B1 | 6/2001 | Ravenscroft et al. |
| 6,254,642 B1 | 7/2001 | Taylor |
| 6,258,120 B1 | 7/2001 | McKenzie et al. |
| 6,264,700 B1 | 7/2001 | Kilcoyne et al. |
| 6,287,334 B1 | 9/2001 | Moll et al. |
| 6,302,917 B1 | 10/2001 | Dua et al. |
| 6,358,197 B1 | 3/2002 | Silverman et al. |
| 6,416,522 B1 | 7/2002 | Strecker |
| 6,425,916 B1 | 7/2002 | Garrison et al. |
| 6,454,785 B2 | 9/2002 | De Hoyos Garza |
| 6,460,543 B1 | 10/2002 | Forsell |
| 6,461,366 B1 | 10/2002 | Seguin |
| 6,494,888 B1 | 12/2002 | Laufer et al. |
| 6,494,895 B2 | 12/2002 | Addis |
| 6,503,264 B1 | 1/2003 | Birk |
| 6,506,196 B1 | 1/2003 | Laufer et al. |
| 6,527,784 B2 | 3/2003 | Adams et al. |
| 6,540,789 B1 | 4/2003 | Silverman et al. |
| 6,544,291 B2 | 4/2003 | Taylor |
| 6,547,801 B1 | 4/2003 | Dargent et al. |
| 6,558,400 B2 | 5/2003 | Deem et al. |
| 6,558,429 B2 | 5/2003 | Taylor |
| 6,572,627 B2 | 6/2003 | Gabbay |
| 6,572,629 B2 | 6/2003 | Kalloo |
| 6,575,896 B2 | 6/2003 | Silverman |
| 6,592,596 B1 | 7/2003 | Geitz et al. |
| 6,596,023 B1 | 7/2003 | Nunez et al. |
| 6,607,555 B2 | 8/2003 | Patterson et al. |
| 6,627,206 B2 | 9/2003 | Lloyd |
| 6,632,227 B2 | 10/2003 | Adams |
| 6,663,639 B1 | 12/2003 | Laufer et al. |
| 6,675,809 B2 | 1/2004 | Stack et al. |
| 6,740,098 B2 | 5/2004 | Abrams et al. |
| 6,740,121 B2 | 5/2004 | Geitz |
| 6,746,460 B2 | 6/2004 | Gannoe et al. |
| 6,755,869 B2 | 6/2004 | Geitz |
| 6,764,518 B2 | 7/2004 | Godin |
| 6,773,440 B2 | 8/2004 | Gannoe et al. |
| 6,773,441 B1 | 8/2004 | Laufer et al. |
| 6,790,214 B2 | 9/2004 | Kraemer et al. |
| 6,790,237 B2 | 9/2004 | Stinson |
| 6,821,285 B2 | 11/2004 | Laufer et al. |
| 6,835,200 B2 | 12/2004 | Laufer et al. |
| 6,845,776 B2 | 1/2005 | Stack et al. |
| 6,916,332 B2 | 7/2005 | Adams |
| 6,932,838 B2 | 8/2005 | Schwartz et al. |
| 6,960,233 B1 | 11/2005 | Berg et al. |
| 6,966,875 B1 | 11/2005 | Longobardi |
| 6,981,978 B2 | 1/2006 | Gannoe |
| 6,981,980 B2 | 1/2006 | Sampson et al. |
| 6,994,715 B2 | 2/2006 | Gannoe et al. |
| 7,011,094 B2 | 3/2006 | Rapackie et al. |
| 7,020,531 B1 | 3/2006 | Colliou et al. |
| 7,025,791 B2 | 4/2006 | Levine et al. |
| 7,033,373 B2 | 4/2006 | de la Torre et al. |

(56) References Cited

U.S. PATENT DOCUMENTS

| | | |
|---|---|---|
| 7,033,384 B2 | 4/2006 | Gannoe et al. |
| 7,037,344 B2 | 5/2006 | Kagan et al. |
| 7,056,305 B2 | 6/2006 | Garza |
| 7,066,945 B2 | 6/2006 | Hashiba et al. |
| 7,083,629 B2 | 8/2006 | Weller et al. |
| 7,090,699 B2 | 8/2006 | Geitz |
| 7,097,650 B2 | 8/2006 | Weller et al. |
| 7,097,665 B2 | 8/2006 | Stack et al. |
| 7,111,627 B2 | 9/2006 | Stack et al. |
| 7,112,186 B2 | 9/2006 | Shah |
| 7,120,498 B2 | 10/2006 | Imran et al. |
| 7,121,283 B2 | 10/2006 | Stack et al. |
| 7,146,984 B2 | 12/2006 | Stack et al. |
| 7,147,140 B2 | 12/2006 | Wukusick et al. |
| 7,152,607 B2 | 12/2006 | Stack et al. |
| 7,160,312 B2 | 1/2007 | Saadat et al. |
| 7,172,613 B2 | 2/2007 | Wazne |
| 7,175,638 B2 | 2/2007 | Gannoe et al. |
| 7,175,660 B2 | 2/2007 | Cartledge et al. |
| 7,211,114 B2 | 5/2007 | Bessler et al. |
| 7,214,233 B2 | 5/2007 | Gannoe et al. |
| 7,220,237 B2 | 5/2007 | Gannoe et al. |
| 7,220,284 B2 | 5/2007 | Kagan et al. |
| 7,223,277 B2 | 5/2007 | DeLegge |
| 7,229,428 B2 | 6/2007 | Gannoe et al. |
| 7,229,453 B2 | 6/2007 | Anderson et al. |
| 7,255,675 B2 | 8/2007 | Gertner et al. |
| 7,261,722 B2 | 8/2007 | McGuckin, Jr. et al. |
| 7,288,101 B2 | 10/2007 | Deem et al. |
| 7,306,614 B2 | 12/2007 | Weller et al. |
| 7,315,509 B2 | 1/2008 | Jeong et al. |
| 7,316,716 B2 | 1/2008 | Egan |
| 7,320,696 B2 | 1/2008 | Gazi et al. |
| 7,326,207 B2 | 2/2008 | Edwards |
| 7,335,210 B2 | 2/2008 | Smit |
| 7,347,863 B2 | 3/2008 | Rothe et al. |
| 7,347,875 B2 | 3/2008 | Levine et al. |
| 7,354,454 B2 | 4/2008 | Stack et al. |
| 7,399,304 B2 | 7/2008 | Gambale et al. |
| 7,431,725 B2 | 10/2008 | Stack et al. |
| 7,461,767 B2 | 12/2008 | Viola et al. |
| 7,470,251 B2 | 12/2008 | Shah |
| 7,485,142 B2 | 2/2009 | Milo |
| 7,503,922 B2 | 3/2009 | Deem et al. |
| 7,520,884 B2 | 4/2009 | Swanstrom et al. |
| 7,575,586 B2 | 8/2009 | Berg et al. |
| 7,608,114 B2 | 10/2009 | Levine et al. |
| 7,615,064 B2 | 11/2009 | Bjerken |
| 7,628,821 B2 | 12/2009 | Stack et al. |
| 7,674,271 B2 | 3/2010 | Bjerken |
| 7,695,446 B2 | 4/2010 | Levine et al. |
| 7,819,836 B2 | 10/2010 | Levine et al. |
| 7,846,138 B2 | 12/2010 | Dann et al. |
| 7,846,174 B2 | 12/2010 | Baker et al. |
| 7,881,797 B2 | 2/2011 | Griffin et al. |
| 7,892,214 B2 | 2/2011 | Kagan et al. |
| 7,892,292 B2 | 2/2011 | Stack et al. |
| 2001/0011543 A1 | 8/2001 | Forsell |
| 2001/0020189 A1 | 9/2001 | Taylor |
| 2001/0020190 A1 | 9/2001 | Taylor |
| 2001/0021796 A1 | 9/2001 | Silverman et al. |
| 2001/0044595 A1 | 11/2001 | Reydel et al. |
| 2002/0022851 A1 | 2/2002 | Kalloo et al. |
| 2002/0055757 A1 | 5/2002 | Torre et al. |
| 2002/0072761 A1 | 6/2002 | Abrams et al. |
| 2002/0082621 A1 | 6/2002 | Shurr et al. |
| 2002/0099439 A1 | 7/2002 | Schwartz et al. |
| 2002/0183767 A1 | 12/2002 | Adams et al. |
| 2002/0183768 A1 | 12/2002 | Deem et al. |
| 2003/0009236 A1 | 1/2003 | Godin |
| 2003/0040804 A1 | 2/2003 | Stack et al. |
| 2003/0040808 A1 | 2/2003 | Stack et al. |
| 2003/0065359 A1 | 4/2003 | Weller et al. |
| 2003/0093117 A1 | 5/2003 | Saadat |
| 2003/0109892 A1 | 6/2003 | Deem et al. |
| 2003/0109931 A1 | 6/2003 | Geitz |
| 2003/0120289 A1 | 6/2003 | McGuckin, Jr. et al. |
| 2003/0158569 A1 | 8/2003 | Wazne |
| 2003/0191476 A1 | 10/2003 | Smit |
| 2003/0191525 A1 | 10/2003 | Thornton |
| 2003/0199989 A1 | 10/2003 | Stack et al. |
| 2003/0199990 A1 | 10/2003 | Stack et al. |
| 2003/0199991 A1 | 10/2003 | Stack et al. |
| 2003/0208209 A1 | 11/2003 | Gambale et al. |
| 2003/0220660 A1 | 11/2003 | Kortenbach et al. |
| 2004/0006351 A1 | 1/2004 | Gannoe et al. |
| 2004/0024386 A1 | 2/2004 | Deem et al. |
| 2004/0030347 A1 | 2/2004 | Gannoe et al. |
| 2004/0039452 A1* | 2/2004 | Bessler ............... 623/23.65 |
| 2004/0044353 A1 | 3/2004 | Gannoe |
| 2004/0044354 A1 | 3/2004 | Gannoe et al. |
| 2004/0044357 A1 | 3/2004 | Gannoe et al. |
| 2004/0044364 A1 | 3/2004 | DeVries et al. |
| 2004/0082963 A1 | 4/2004 | Gannoe et al. |
| 2004/0088023 A1 | 5/2004 | Imran et al. |
| 2004/0092892 A1 | 5/2004 | Kagan et al. |
| 2004/0092974 A1 | 5/2004 | Gannoe et al. |
| 2004/0093091 A1 | 5/2004 | Gannoe et al. |
| 2004/0098043 A1 | 5/2004 | Trout |
| 2004/0107004 A1 | 6/2004 | Levine et al. |
| 2004/0117031 A1 | 6/2004 | Stack et al. |
| 2004/0138761 A1 | 7/2004 | Stack et al. |
| 2004/0143342 A1 | 7/2004 | Stack et al. |
| 2004/0148034 A1 | 7/2004 | Kagan et al. |
| 2004/0153167 A1 | 8/2004 | Stack et al. |
| 2004/0158331 A1 | 8/2004 | Stack et al. |
| 2004/0162568 A1 | 8/2004 | Saadat et al. |
| 2004/0172141 A1 | 9/2004 | Stack et al. |
| 2004/0172142 A1 | 9/2004 | Stack et al. |
| 2004/0186502 A1 | 9/2004 | Sampson et al. |
| 2004/0210243 A1 | 10/2004 | Gannoe et al. |
| 2004/0215216 A1 | 10/2004 | Gannoe et al. |
| 2004/0220682 A1 | 11/2004 | Levine et al. |
| 2004/0225183 A1 | 11/2004 | Michlitsch et al. |
| 2004/0225305 A1 | 11/2004 | Ewers et al. |
| 2004/0236419 A1 | 11/2004 | Milo |
| 2004/0243152 A1 | 12/2004 | Taylor et al. |
| 2004/0243223 A1 | 12/2004 | Kraemer et al. |
| 2004/0267378 A1 | 12/2004 | Gazi et al. |
| 2005/0004430 A1 | 1/2005 | Lee et al. |
| 2005/0004681 A1 | 1/2005 | Stack et al. |
| 2005/0033326 A1 | 2/2005 | Briganti et al. |
| 2005/0033345 A1 | 2/2005 | DeLegge |
| 2005/0049718 A1 | 3/2005 | Dann et al. |
| 2005/0075654 A1 | 4/2005 | Kelleher |
| 2005/0080444 A1 | 4/2005 | Kraemer et al. |
| 2005/0085787 A1 | 4/2005 | Laufer et al. |
| 2005/0096673 A1 | 5/2005 | Stack et al. |
| 2005/0096750 A1 | 5/2005 | Kagan et al. |
| 2005/0149114 A1 | 7/2005 | Cartledge et al. |
| 2005/0159769 A1 | 7/2005 | Alverdy |
| 2005/0177181 A1 | 8/2005 | Kagan et al. |
| 2005/0183732 A1 | 8/2005 | Edwards |
| 2005/0192599 A1 | 9/2005 | Demarais |
| 2005/0192615 A1 | 9/2005 | Torre et al. |
| 2005/0216040 A1 | 9/2005 | Gertner et al. |
| 2005/0216042 A1 | 9/2005 | Gertner |
| 2005/0240279 A1 | 10/2005 | Kagan et al. |
| 2005/0247320 A1 | 11/2005 | Stack et al. |
| 2005/0250980 A1 | 11/2005 | Swanstrom et al. |
| 2005/0251158 A1 | 11/2005 | Sadat et al. |
| 2005/0251162 A1 | 11/2005 | Rothe et al. |
| 2005/0256533 A1 | 11/2005 | Roth et al. |
| 2005/0256587 A1 | 11/2005 | Egan |
| 2005/0261712 A1 | 11/2005 | Balbierz et al. |
| 2005/0267405 A1 | 12/2005 | Shah |
| 2005/0267499 A1 | 12/2005 | Stack et al. |
| 2005/0267595 A1 | 12/2005 | Chen et al. |
| 2005/0267596 A1 | 12/2005 | Chen et al. |
| 2005/0273060 A1 | 12/2005 | Levy et al. |
| 2006/0015006 A1 | 1/2006 | Laurence et al. |
| 2006/0020278 A1 | 1/2006 | Burnett et al. |
| 2006/0058829 A1 | 3/2006 | Sampson et al. |
| 2006/0129094 A1 | 6/2006 | Shah |

(56) References Cited

U.S. PATENT DOCUMENTS

| | | |
|---|---|---|
| 2006/0151568 A1 | 7/2006 | Weller et al. |
| 2006/0155259 A1 | 7/2006 | MacLay |
| 2006/0155311 A1 | 7/2006 | Hashiba et al. |
| 2006/0178560 A1 | 8/2006 | Saadat et al. |
| 2006/0178691 A1 | 8/2006 | Binmoeller |
| 2006/0195139 A1 | 8/2006 | Gertner |
| 2006/0253142 A1 | 11/2006 | Bjerken |
| 2006/0271076 A1 | 11/2006 | Weller et al. |
| 2006/0282095 A1 | 12/2006 | Stokes et al. |
| 2006/0287734 A1 | 12/2006 | Stack et al. |
| 2007/0010864 A1 | 1/2007 | Dann et al. |
| 2007/0032800 A1 | 2/2007 | Ortiz et al. |
| 2007/0043384 A1 | 2/2007 | Ortiz et al. |
| 2007/0055292 A1 | 3/2007 | Ortiz et al. |
| 2007/0060932 A1 | 3/2007 | Stack et al. |
| 2007/0149994 A1 | 6/2007 | Sosnowski et al. |
| 2007/0175488 A1 | 8/2007 | Cox et al. |
| 2007/0191870 A1 | 8/2007 | Baker et al. |
| 2007/0191871 A1 | 8/2007 | Baker et al. |
| 2007/0198074 A1 | 8/2007 | Dann et al. |
| 2007/0219571 A1 | 9/2007 | Balbierz et al. |
| 2007/0239284 A1 | 10/2007 | Skerven et al. |
| 2007/0260327 A1 | 11/2007 | Case et al. |
| 2007/0276432 A1 | 11/2007 | Stack et al. |
| 2008/0033574 A1 | 2/2008 | Bessler et al. |
| 2008/0065122 A1 | 3/2008 | Stack et al. |
| 2008/0116244 A1 | 5/2008 | Rethy et al. |
| 2008/0190989 A1 | 8/2008 | Crews et al. |
| 2008/0195226 A1 | 8/2008 | Williams et al. |
| 2008/0208355 A1 | 8/2008 | Stack et al. |
| 2008/0208356 A1 | 8/2008 | Stack et al. |
| 2008/0269797 A1 | 10/2008 | Stack et al. |
| 2008/0294179 A1 | 11/2008 | Balbierz et al. |
| 2009/0018558 A1 | 1/2009 | Laufer et al. |
| 2009/0024143 A1 | 1/2009 | Crews et al. |
| 2009/0030284 A1 | 1/2009 | Cole et al. |
| 2009/0125040 A1 | 5/2009 | Hambley et al. |
| 2009/0171383 A1 | 7/2009 | Cole et al. |
| 2009/0177215 A1 | 7/2009 | Stack et al. |
| 2009/0236388 A1 | 9/2009 | Cole et al. |
| 2009/0236389 A1 | 9/2009 | Cole et al. |
| 2009/0236390 A1 | 9/2009 | Cole et al. |
| 2009/0236391 A1 | 9/2009 | Cole et al. |
| 2009/0236392 A1 | 9/2009 | Cole et al. |
| 2009/0236394 A1 | 9/2009 | Cole et al. |
| 2009/0236396 A1 | 9/2009 | Cole et al. |
| 2009/0236397 A1 | 9/2009 | Cole et al. |
| 2009/0236398 A1 | 9/2009 | Cole et al. |
| 2009/0236400 A1 | 9/2009 | Cole et al. |
| 2009/0236401 A1 | 9/2009 | Cole et al. |

FOREIGN PATENT DOCUMENTS

| | | |
|---|---|---|
| EP | 1492478 | 1/2005 |
| EP | 1602336 | 12/2005 |
| FR | 2768324 | 3/1999 |
| JP | 09-168597 | 6/1997 |
| WO | WO 91/01117 A1 | 2/1991 |
| WO | WO 97/47231 | 12/1997 |
| WO | WO 00/12027 | 3/2000 |
| WO | WO 00/32137 A1 | 6/2000 |
| WO | WO 00/78227 | 12/2000 |
| WO | WO 01/41671 | 6/2001 |
| WO | WO 01/45485 | 6/2001 |
| WO | WO 01/49359 | 7/2001 |
| WO | WO 01/66018 | 9/2001 |
| WO | WO 01/85034 | 11/2001 |
| WO | WO 01/89393 | 11/2001 |
| WO | WO 02/060328 | 8/2002 |
| WO | WO 03/017882 | 3/2003 |
| WO | WO 03/086246 | 10/2003 |
| WO | WO 03/086247 | 10/2003 |
| WO | WO 03/090633 | 11/2003 |
| WO | WO 03/094784 A2 | 11/2003 |
| WO | WO 03/094785 | 11/2003 |
| WO | WO 03094785 A1 * | 11/2003 |
| WO | WO 03/099137 | 12/2003 |
| WO | WO 2004/019765 | 3/2004 |
| WO | WO 2004/019787 | 3/2004 |
| WO | WO 2004/032760 | 4/2004 |
| WO | WO 2004/037064 | 5/2004 |
| WO | WO 2004/041133 | 5/2004 |
| WO | WO 2004/064680 | 8/2004 |
| WO | WO 2004/064685 | 8/2004 |
| WO | WO 2004/080336 | 9/2004 |
| WO | WO 2004/110285 | 12/2004 |
| WO | WO 2005/037152 | 4/2005 |
| WO | WO 2005/079673 | 9/2005 |
| WO | WO 2005/096991 | 10/2005 |
| WO | WO 2005/105003 | 11/2005 |
| WO | WO 2006/016894 | 2/2006 |
| WO | WO 2006/055365 | 5/2006 |
| WO | WO 2006/127593 | 11/2006 |
| WO | WO 2007/041598 | 4/2007 |
| WO | WO 2008/030403 | 3/2008 |
| WO | WO 2008/033409 | 3/2008 |
| WO | WO 2008/033474 | 3/2008 |
| WO | WO 2008/141288 | 11/2008 |
| WO | WO 2009/011881 | 1/2009 |
| WO | WO 2009/011882 | 1/2009 |
| WO | WO 2009/086549 | 7/2009 |
| WO | WO 2009/117533 | 9/2009 |
| WO | WO 2010/054399 | 5/2010 |
| WO | WO 2010/054404 | 5/2010 |

OTHER PUBLICATIONS

International Search Report from PCT Patent Application No. PCT/US2003/004449 mailed Aug. 13, 2003.
International Search Report from PCT Patent Application No. PCT/US2004/006695 mailed Sep. 8, 2004.
International Search Report from PCT Patent Application No. PCT/US2004/033007 mailed Feb. 9, 2005.
International Search Report from PCT Patent Application No. PCT/US2005/014372 mailed Jul. 28, 2005.
International Search Report from PCT Patent Application No. PCT/US2006/019727 mailed Apr. 19, 2007.
International Search Report from PCT Patent Application No. PCT/US2006/038684 mailed Feb. 14, 2007.
International Search Report from PCT Patent Application No. PCT/US2007/019227 mailed Feb. 20, 2008.
International Search Report from PCT Patent Application No. PCT/US2007/019833 mailed Feb. 20, 2008.
International Search Report from PCT Patent Application No. PCT/US2007/019940 mailed Mar. 14, 2008.
International Search Report from PCT Patent Application No. PCT/US2008/008726 mailed Oct. 16, 2008.
International Search Report from PCT Patent Application No. PCT/US2008/008729 mailed Aug. 18, 2009.
International Search Report from PCT Patent Application No. PCT/US2008/063440 mailed Aug. 1, 2008.
International Search Report from PCT Patent Application No. PCT/US2008/088581 mailed Feb. 26, 2009.
International Search Report from PCT Patent Application No. PCT/US2009/037586 mailed Sep. 28, 2009.
International Search Report from PCT Patent Application No. PCT/US2009/063925 mailed Jan. 12, 2010.
International Search Report from PCT Patent Application No. PCT/US2009/063930 mailed Jan. 12, 2010.
Felsher, et al., "Mucosal apposition in endoscopic suturing", Gastrointestinal Endoscopy, vol. 58, No. 6, pp. 867-870, (2003).
Stecco, et al., "Trans-oral plication formation and gastric implant placement in a canine model", Stecco Group, San Jose and Barosense, Inc., Redwood City, CA (2004).
Stecco, et al. "Safety of a gastric restrictive implant in a canine model", Stecco group, San Jose amd Barosense, Inc., Redwood City, CA (2004).

* cited by examiner

SATIATION DEVICES AND METHODS

This application is a continuation of U.S. patent application Ser. No. 10/345,914, filed Jan. 16, 2003, now abandoned, which is a continuation-in-part of U.S. patent application Ser. No. 09/940,110, filed Aug. 27, 2001, now U.S. Pat. No. 6,675,809, and is a continuation-in-part of U.S. application Ser. No. 10/118,289, filed Apr. 8, 2002, now U.S. Pat. No. 6,845,776, and which also claims the benefit of U.S. Provisional Application No. 60/379,306, filed May 10, 2002.

FIELD OF THE INVENTION

The present invention relates generally to the field of devices and methods for achieving weight loss in humans, and specifically to the use of devices implantable within the human stomach for controlling feelings of hunger and/or limiting food intake.

BACKGROUND OF THE INVENTION

Various medical approaches are used for controlling obesity. These approaches include diet, medication, and surgical procedures. One of the more successful surgical procedures is the vertical gastroplexy or proximal gastric pouch procedure in which a portion of the proximal stomach is formed into a small pouch with a small opening into the remainder of the stomach. This proximal gastric pouch may include a Roux-en-Y anastomosis in which a portion of the jejunum is connected to the pouch so as to shunt food from the proximal region of the stomach into the intestine, thereby minimizing absorption of food into the bloodstream. However, known complications are present with each of these procedures and more successful options are desired.

Other alternatives include implantation of gastric balloons that prevent overeating by occupying volume within the stomach. Unfortunately, gastric balloons can migrate down the GI tract, causing obstruction and thus necessitating removal.

It is therefore desirable to provide a successful and minimally-invasive alternative to existing approaches for controlling obesity.

SUMMARY OF THE INVENTION

A satiation device utilizing principles of the present invention includes a sheath or liner positioned within the stomach. Food ingested by the patient passes through the sheath or liner, thereby minimizing contact between the ingested food and the stomach. It is believed that over time, reduced contact between food and the stomach will result in decreased Ghrelin production by the patient and a consequent decrease in appetite. In some embodiments, the satiation device may also include a proximal pouch and/or a distal bypass tube.

DETAILED DESCRIPTION

Figure 1:
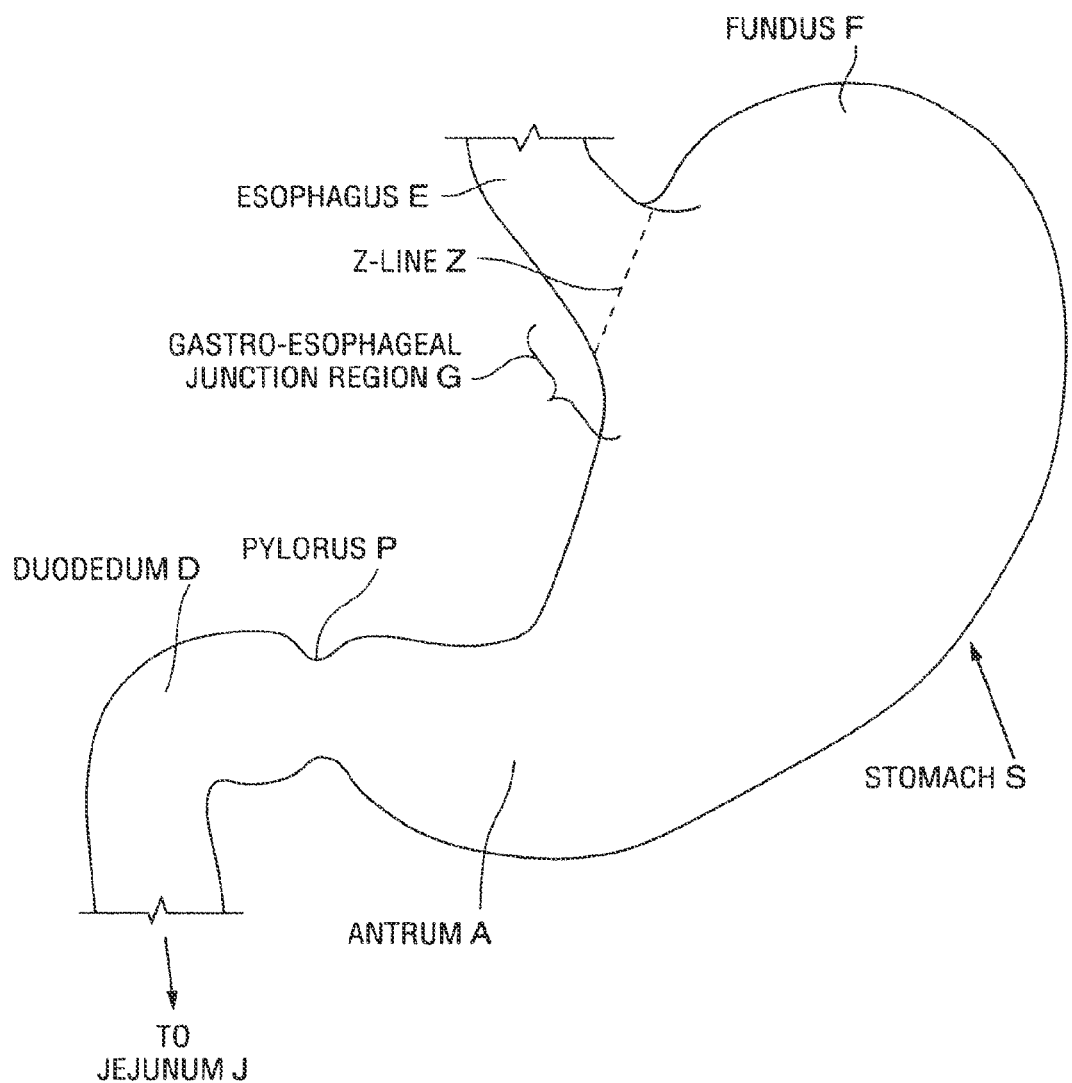
FIG. 1 is a schematic illustration of a human stomach and a portion of the small intestine.

An anatomical view of a human stomach S and associated features is shown in FIG. 1. The esophagus E delivers food from the mouth to the stomach S. The z-line or gastro-esophageal junction Z is the irregularly-shaped border between the thin tissue of the esophagus and the thicker tissue of the stomach wall. The gastro-esophageal junction region G is the region encompassing the distal portion of the esophagus E, the z-line, and the proximal portion of the stomach S.

Stomach S includes a fundus F at its proximal end and an antrum A at its distal end. Antrum A feeds into the pylorus P which attaches to the duodenum D, the proximal region of the small intestine. Within the pylorus P is a sphincter that prevents backflow of food from the duodenum D into the stomach. The middle region of the small intestine, positioned distally of the duodenum D, is the jejunum J.

Ghrelin is a satiety hormone secreted by cells in the stomach and the small intestine. Increased production of Ghrelin, such as before a meal, causes a person to experience hunger. After the person has eaten, production of Ghrelin decreases. It is presently believed that 85% of the Ghrelin-secreting cells are found in the stomach, and that the remaining 15% are in the antrum and small intestine. Obese patients have been found to possess significantly higher Ghrelin levels than non-obese patients. Moreover, recent studies have found that a patient's production of Ghrelin decreases significantly following gastric bypass procedures such as the Roux-en-y procedure described above. Various versions of the embodiments described herein provide an exclusion sleeve or liner situated within the stomach and extending from the proximal or middle stomach to the distal stomach or the small intestine. Over time, the presence of the exclusion sleeve will cause the Ghrelin-secreting cells to decrease Ghrelin production, causing the level of hunger experienced by a patient to decrease and thus resulting in weight loss by the patient.

Some of the embodiments of exclusion sleeves also include a pouch or funnel positioned at the gastro-esophageal junction region so as to form a small reservoir which collects masticated food from the esophagus. The pouch may limit the amount of food that can be consumed at one time. Additionally or alternatively, as the pouch fills with food, it may distend, imparting pressure against the upper stomach and lower esophageal sphincter causing the patient to experience sensations of fullness. Over time the food within this reservoir descends into the exclusion sleeve through a distal opening in the pouch. The pouch may optionally include a proximal tubular extension positionable within the esophagus to facilitate flow of food from the esophagus into the pouch. Various pouches of a type suitable for use with the exclusion sleeve are described in U.S. application Ser. No. 10/118,289, filed Apr. 8, 2002, which is hereby incorporated by reference for all purposes.

The devices may be modular in that where multiple components (e.g. a sleeve and pouch) are to be implanted, the various components may be provided separately from one another. In such a modular system, the separately implanted components may be attached to one another within the body during implantation, or certain ones of them may remain unattached to one another even after implantation. Alternatively, the physician may assemble the components to one another just prior to implantation. Modular components are desirable in that they permit the physician to select sizes for each component that are appropriate for the patient.

Implantation of the described devices is preferably performed endoscopically, by passing the devices through the esophagus, preferably under endoscopic visualization. Alternatively, the devices may be implanted using surgical or laparoscopic procedures.

Figure 2A:
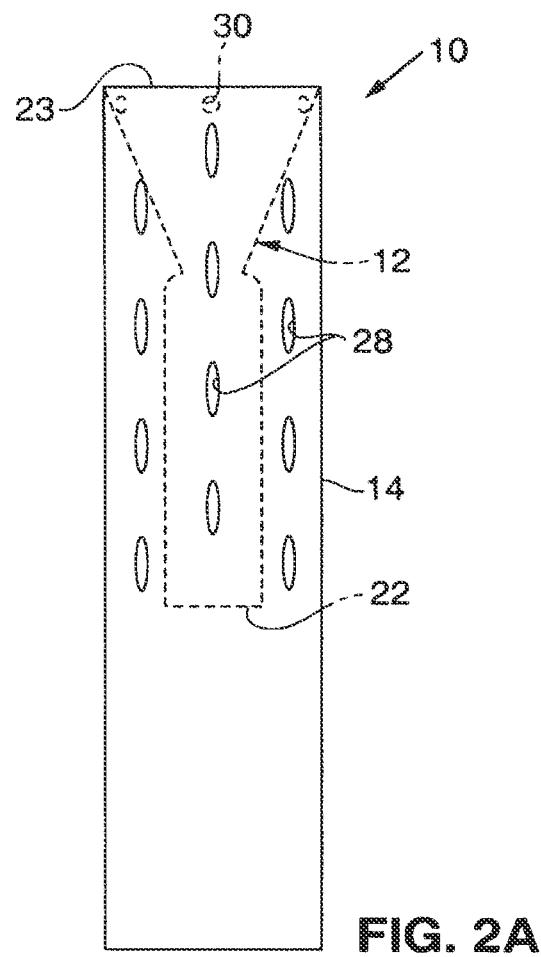
FIG. 2A is a side elevation view of a first embodiment of a satiation device.

One embodiment of a satiation device is illustrated in FIG. 2A and includes a pouch 12 positioned within an elongate exclusion sleeve 14. For the purposes of this application, the term "satiation devices" will be used to mean devices intended to induce weight loss in one or more of a variety of ways. These include, but are not limited to, physically restricting the amount of food that can be consumed, and/or imparting pressure against portions of the body (e.g. stomach, esophagus, esophageal sphincter, etc) causing the patient to experience sensations of fullness, and/or affecting levels of hormones or other substances in the body that control or affect feelings of hunger, and/or affecting the amount of ingested food absorbed by the body.

Figure 2B:
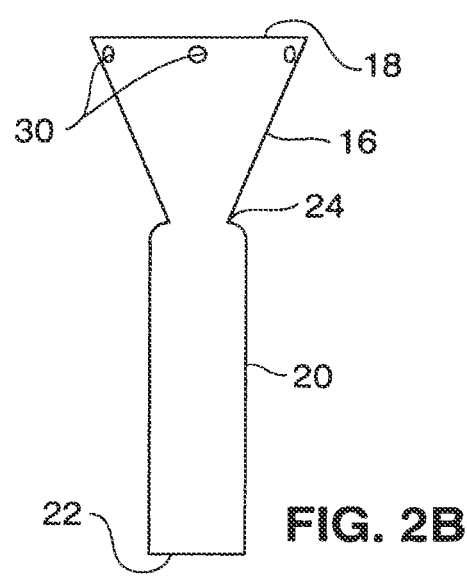
FIG. 2B is a side elevation view of the pouch and chute of the embodiment of FIG. 2A.
Figure 3:
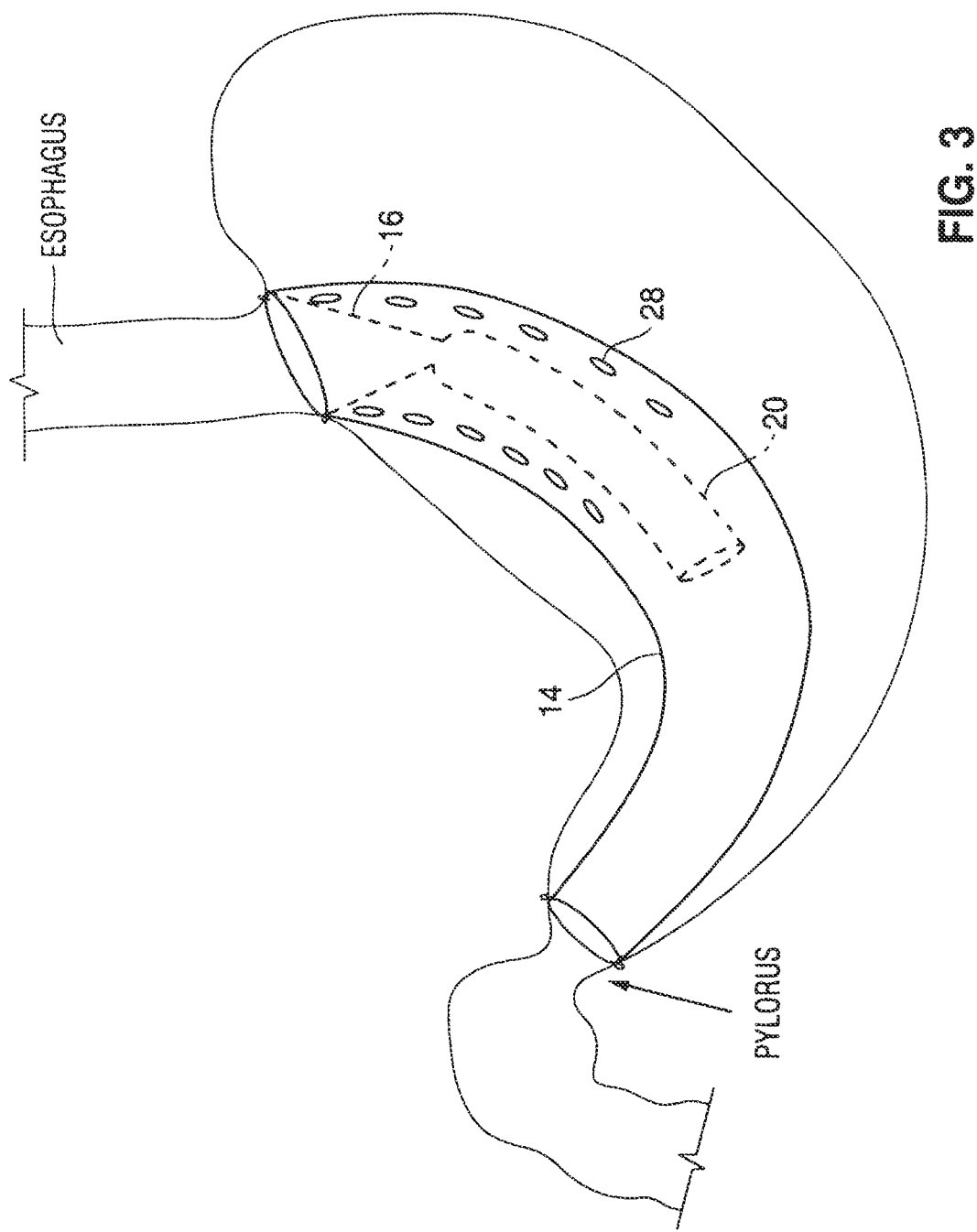
FIG. 3 is a schematic illustration of a human stomach illustrating in vivo positioning of the embodiment of FIG. 2A.

Pouch 12, shown without the sleeve in FIG. 2B, includes a funnel-shaped proximal portion 16 with an opening 18 that is positionable at the gastro-esophageal junction region (and preferably below the z-line) as shown in FIG. 3. Although a funnel shape is preferred here, a variety of alternative shapes may be used for the proximal portion of the pouch. For example, the pouch may have a much shorter proximal-to-distal dimension and thus take the shape of a shallow saucer with a small hole on its bottom surface. Other examples include, but are not limited to, egg shapes, other tapered shapes such as the shape of a "spinning top", cylindrical shapes, and other symmetrical or asymmetrical shapes.

Because of its small volume (which may be on the order of approximately 2 cc-300 cc in volume, but is preferably in the range of 10-30 cc), the pouch functions to limit the amount of food that can be consumed at one time. Over time the food within this reservoir descends into the exclusion sleeve 14 through a distal opening in the pouch.

A distal chute 20 extends from the funnel-shaped proximal portion 16 and includes a distal opening 22. In this embodiment, the chute 20 tapers outwardly from the funnel 16 to form a valve 24 between the funnel and chute. The valve 24 may be formed of an elastic material that permits the valve opening to increase in size to permit large pieces of food to pass through. If desired, he diameter of the valve 24 may be adjustable by endoscopic means, such as by tightening a ligature around the valve, inflating an inflatable cuff positioned around the valve, or using various other means. This increases the effectiveness of the pouch by decreasing the exit diameter—thereby causing food to exit the pouch more slowly and prolonging the feeling of fullness experienced by the patient. Likewise, the diameter of the valve 24 may be endoscopically increased by deflating a fluid filled restrictive cuff, using a tool to cut or stretch open the valve, or using various other means, to increase the ability of the patient to tolerate the pouch by permitting more rapid emptying of the pouch.

Pouch 12 may be formed of a flexible material that will prevent passage of food through the sides of the pouch. Examples of such materials include, but are not limited to polyesters (e.g. Dacron® polyester), ePTFE fabric (e.g. GoreTex® fabric or others), a polyurethane such as ChronoFlex® polyurethane, nylon fabrics, silicone, other polymeric materials, and bio-absorbable materials (e.g. PLLA, PGA, PCL, poly-amhydride etc). The pouch may be formed of a composite of compliant, semi-compliant and/or non-compliant materials which give different regions of the pouch different degrees of compliance so as to allow/limit expansion of the pouch in various locations. For example, it may be desirable to provide the pouch with a fairly elastic exit port to as to prevent occlusion in the event a large piece of food is ingested and/or to control the exit pressure of food from the pouch, whereas the proximal end of the pouch may be stiffer to prevent bulging. Varying degrees of compliance may also be built into the pouch by varying the cross-sectional thickness in different regions of the pouch. The material may be coated with a lubricious, bio-compatible, chemically inert material, such as paraleyne, to reduce friction on the base material's surface which will help prevent sticking and food build up on the device.

Sleeve 14 is a flexible tube having a proximal opening 23 and a distal opening 26. The sleeve material may be similar to the material described with respect to the pouch 12, but should be sufficiently flexible to permit peristalsis. The exterior of the sleeve material may be impregnated with substances known to inhibit release of Ghrelin or other hormones associated with feelings of satiety. Such substances may be chemical or pharmaceutical substances, therapeutic molecules or cells, or genetic material. The sleeve may also be impregnated with an acid to inhibit production of Gastrin, or its exterior may be impregnated with an anti-Gastrin antibody.

The sleeve 14 and pouch 12 are preferably attached to one another at their respective proximal openings 18, 23 using sutures, clips, adhesives or other suitable means. These components may be attached to one another during manufacture or just prior to implantation, or they may be separately implanted.

The proximal portion of the sleeve 14 contains a plurality of openings 28 sized to allow gastric secretions to enter the sleeve 14 to aid in digesting food that has passed from the pouch 12 into the sleeve 14 and to allow drainage of the secretions from the stomach. The stomach secretions exit the stomach via the sleeve and drain into the pylorus. The openings 28 may take the form of perforations or slots in the sleeve wall. Alternatively, the openings may take the form of apertures in mesh or porous regions in a portion of the sleeve. For example, ePTFE with an open cell structure is a material that can be constructed to allow gastric secretions to enter without allowing food to exit.

In the embodiment shown in FIG. 3, the openings are positioned such that when the pouch 12 is positioned within the sleeve 14 for use, the distal opening 22 of the chute 20 is preferably distal to the openings 28 so as to prevent food from exiting the sleeve through the openings 28. The openings 28 may be positioned in any other locations as well, particularly if the openings are small enough to prevent food from passing through. Examples of alternative locations for the openings include locations near the distal end of the sleeve (see FIG. 4), or locations substantially along the entire sleeve length.

The diameter of the sleeve 14 is sufficiently large to allow the pouch to be enclosed within the sleeve 14, but is preferably sufficiently narrow to permit acids produced within the stomach to flow into contact with the walls of the antrum. It is believed that such contact is needed for normal regulation of the hormone Gastrin. Gastrin is a physiological regulator of gastric acid secretion within the stomach. Increased Gastrin levels result in increased secretion of gastric acids. Acid levels that are too high can produce ulcers.

Secretion of Gastrin (and thus resultant secretion of gastric acids) is inhibited when cells in the antrum detect a low pH. It is thus important for acids in the stomach to contact the antrum to ensure normal regulation of Gastrin. If the acids are not permitted to contact the antrum, Gastrin production would increase, and might thus cause an increased production of gastric acids that could lead to stomach ulcers.

Methods for implanting satiation devices such as pouch 12 are shown and described in U.S. application Ser. No. 10/118, 289 filed Apr. 8, 2002. For example, some of the disclosed methods involve packaging the satiation device within a deployment tube, inserting the distal end of the tube into the stomach (preferably from the esophagus), ejecting the satiation device from the tube using a pushrod passed through tube, and then securing the satiation device using sutures, clips, adhesives, radial forces, stents or stent-like structures, etc. Such methods may be utilized to deploy the satiation devices described herein, including the pouch 12 and sleeve 14.

During implantation the pouch 12 is secured at the gastroesophageal junction region G using sutures, clips, adhesives, stents or stent-like structures, or other suitable means. One suture attachment device found useful for applying sutures between the pouch and tissue is the "Sew-Right" suturing device available from LSI Solutions of Victor, N.Y.

Although the pouch may be secured to the esophageal tissue, it is more preferable to apply sutures/clips below the Z-line to allow for attachment to the thicker tissue of the stomach wall. Suture attachment points, which may take the form of holes, anchor loops, eyelets, windows, or grommets 30 in the pouch may be used to provide regions (which may be reinforced) for anchoring the sutures. Although as few or as many of such suture/clip attachment points as needed may be used, at least four such points are desirable, such as at 90.degree. intervals around the pouch, so as to enable the pouch to be secured around the full circumference of the tissue. The suture attachment points may be made of a suitably dense radio-opaque material, such as titanium or gold, to add in visualization of the device during or after the procedure. Each suture attachment point may also be marked using a different color to facilitate identification and orientation of sutures. If the pouch is formed of a less durable material, the proximal portion of the pouch (in which the eyelets 30 are located) may be formed of more durable material such as a woven material, Dacron® polyester or ePTFE fabric so as to provide a more secure sewing region. Although loops, grommets, eyelets or reinforced regions may be advantageous, the pouch may alternatively be provided without suture attachment points formed of special materials (with or without identifying markings)—in which case the sutures are passed directly through the pouch material.

The flexible pouch and/or sleeve material may be reinforced with, constructed of, or supported by supporting members, such as a soft mesh, a cage structure, ribs, rings etc. The supporting members may be formed of stainless steel, polymer, shape memory materials such as nitinol, shape memory alloys, or shape memory polymers, or thickened regions of material. The pouch and/or sleeve may be constructed so as to be self-expanding, such that the pouch and/or sleeve springs radially open into an expanded condition upon ejection from a deployment device or catheter as described above.

The proximal end of sleeve 14, near proximal opening 23, may be attached to the pouch 12 alone, or it may be attached to the pouch 12 and to the surrounding tissue. The sleeve 14 is attached at its distal opening to the distal stomach (e.g. at the antrum) near the pylorus, so as to allow food exiting the sleeve 14 to flow out of the stomach to the small intestine. Attachment is made using sutures, clips, adhesives, stents or stent-like structures or other suitable means.

Figure 4:
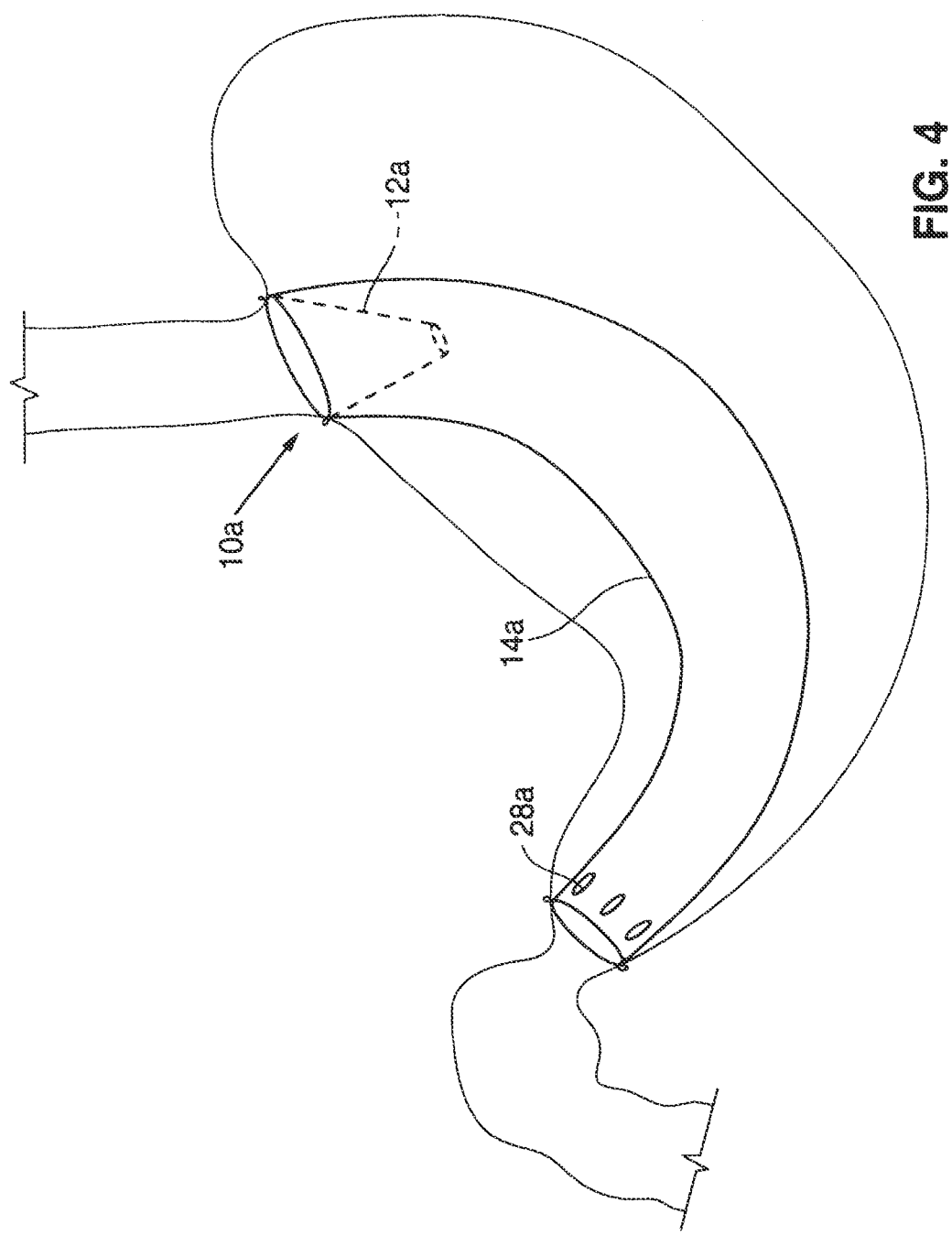
FIG. 4 is a schematic illustration of a human stomach illustrating in vivo positioning of a second embodiment of a satiation device.

FIG. 4 shows an alternative embodiment of a satiation device 10a using a pouch 12a and sleeve 14a. The satiation device 10a differs from that of FIG. 3 primarily in that the pouch 12a is provided without a distal chute (see chute 20 FIG. 3), and in that the openings 28a in the sleeve are positioned at the distal end of the sleeve so as to permit drainage of gastric secretions into the sleeve 28a and from the sleeve into the pylorus. Drainage of gastric secretions is desirable to avoid accumulation of such secretions in the stomach.

The sleeve 14a (and also the sleeve 14 of FIG. 3) may be semi-impermeable, allowing gastric secretions to enter without allowing food to exit. Materials such as ePTFE with open-cell structure (e.g. node to fibril lengths of 20-100 micron) are suitable for this purpose.

The embodiments of FIGS. 3 and 4 are believed to cause weight loss in a number of ways. First, as the pouch fills with food, it may distend, imparting pressure against the upper stomach and lower esophageal sphincter causing the patient to experience sensations of fullness after consuming small quantities of food. Second, it is believed that isolating consumed food from the walls of the stomach using the exclusion sleeve 14, 14a will lead to a temporary increase in the patient's production of Ghrelin followed by a "burn out" phenomenon over time in which the Ghrelin is reduced, in turn leading to decreased sensations of hunger. Third, digestion is delayed and absorption of the food is minimized.

FIGS. 5 through 8 show additional embodiments that also control satiety by isolating consumed food from the walls of the stomach so as to eventually decrease day-to-day production of Ghrelin by the patient due to the above described "burn out" phenomenon. Each of these embodiments includes an exclusion liner that is positioned within the stomach such that consumed food passes through the liner and then exits the liner to flow into the small intestine via the pylorus.

Figure 5:
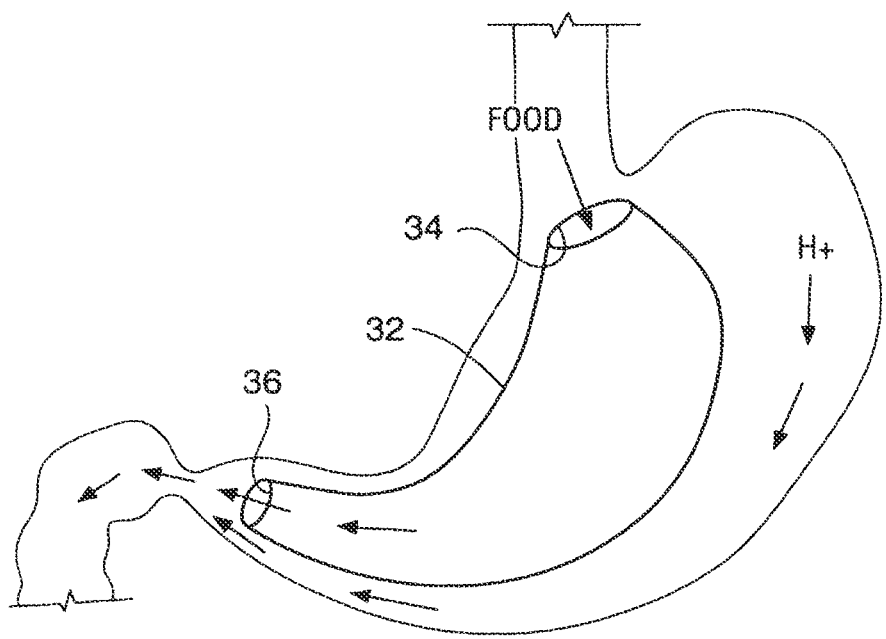
FIG. 5 is a schematic illustration of a human stomach showing in vivo positioning of an exclusion liner

Referring to FIG. 5, a first exclusion liner 32 includes a proximal opening 34 positioned in the proximal stomach, such as at the gastro-esophageal junction region G, and a distal opening 36 positioned in the antrum A, preferably adjacent to the pylorus P. The liner 32 may be proportioned to substantially line the stomach while still allowing clearance for gastric acids (labeled H+ in FIG. 5) to contact the walls of the antrum surrounding the liner—so as to prevent overproduction of Gastrin as described above. Alternatively, the liner may have a significantly narrower diameter if desired. As shown in FIG. 5, liner 32 reduces contact between ingested food and the stomach, including the fundus and the antrum.

The proximal region adjacent to the proximal opening 34 is preferably secured to tissue at the gastro-esophageal junction region below the Z line using sutures, clips, adhesives, stents or stent-like structures or other suitable means. The distal region adjacent to the distal opening may be secured in a leak-proof manner to the distal antrum, or it may be secured more loosely to permit gastric secretions to exit the stomach into the pylorus (see arrows in FIG. 5). For example, clips or sutures, etc. may be applied in a manner that leaves a gap between the distal opening 36 and the pylorus to permit drainage of gastric secretions. Alternatively, if such drainage is desired, the liner 32 may be provided with a plurality of openings (see, for example, openings 28a in FIG. 4) that allow gastric secretions to flow into the liner and then into the pylorus. As another alternative, liner may be supported by a cage structure having resilient cage members that contact the walls of the stomach to prevent migration of the liner within the stomach, but that allow clearance between the stomach walls and the exterior of the liner. Cage structures of a type that may be adapted for this purpose are shown and described in U.S. application Ser. No. 09/940,110, filed Aug. 27, 2001, the entirety of which is incorporated by reference.

Figure 6:
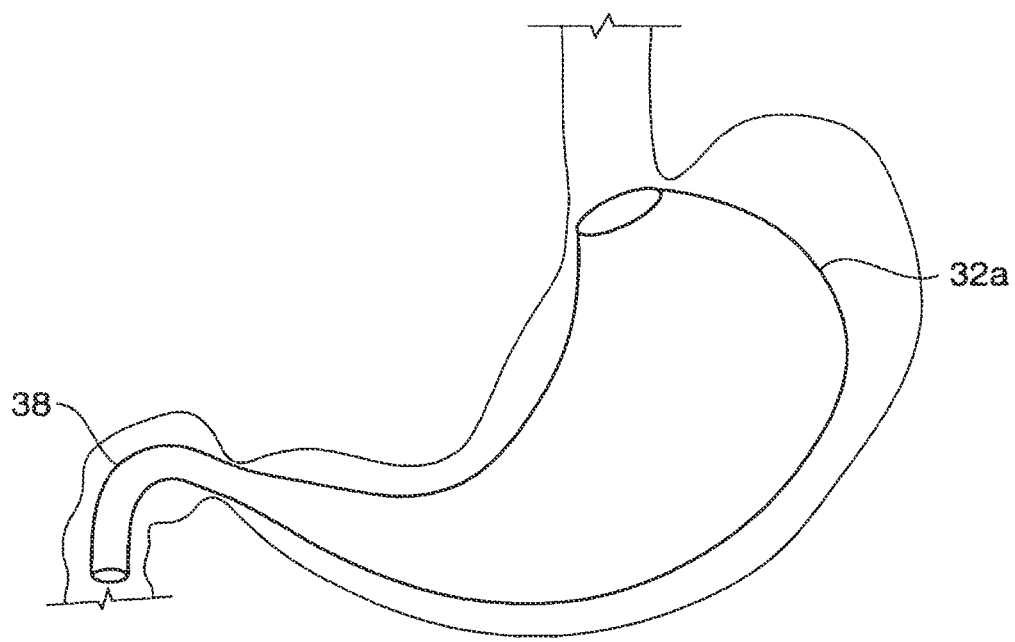
FIG. 6 is a schematic illustration similar to FIG. 5 showing an exclusion liner having a distal tube.

FIG. 6 shows an exclusion liner 32a that is similar to the liner 32 of FIG. 5), but that further includes a distal tube 38 that is secured in the pylorus or duodenum using sutures, anchors, clips, stents or stent-like structures, adhesives, etc. Again, this distal connection may be leak proof to prevent drainage of secretions, or it may configured to allow such drainage.

Figure 7:
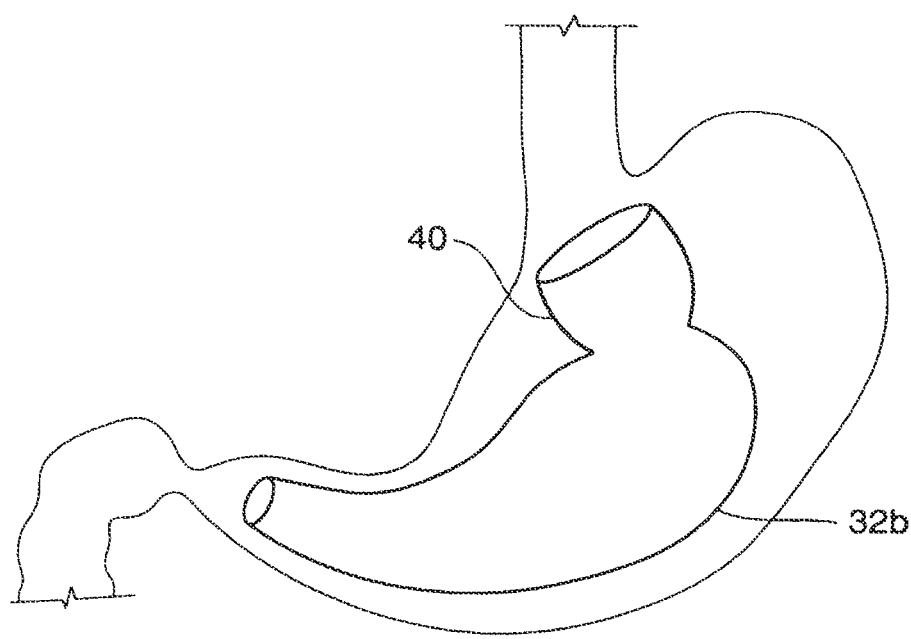
FIG. 7 is a schematic illustration similar to FIG. 5 showing an exclusion liner having a proximal pouch.

FIG. 7 shows an exclusion liner 32b that is similar to the liner of FIG. 5, except that it includes a proximal pouch 40 attachable at the gastro-esophageal junction region. As with the embodiment of FIGS. 3 and 4, the pouch 40 fills with food when the patient eats, causing the patient to experience sensations of fullness after consuming small quantities of food. The pouch 40 may be integral with the liner 32b, or it may be separately attachable prior to or during implantation. As with the embodiments of FIG. 5 and FIG. 6, the distal end of the liner 32b may be attached to the distal antrum in a manner that permits drainage of secretions present outside the liner, or in a manner that occludes such drainage. The embodiment of FIG. 7 may also be provided with a distal tube similar to the distal tube 38 of the FIG. 6 embodiment.

Figure 8:
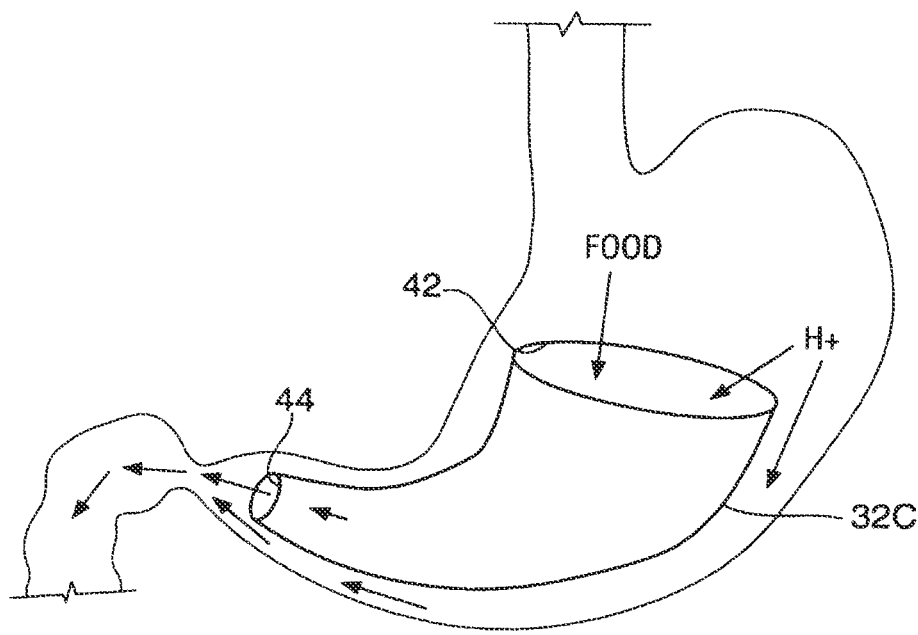
FIG. 8 is a schematic illustration similar to FIG. 5 showing an exclusion liner having a proximal end at the middle stomach/proximal antrum.

FIG. 8 shows an antral exclusion liner 32c proportioned to extend from the middle stomach or the proximal antrum to the distal antrum. Liner 32c includes a large proximal opening 42 and a smaller distal opening 44 as shown. The proximal region of the liner 32c is secured to the surrounding walls of the stomach, and the distal region is secured to the distal antrum. Liner 32c may be secured in a manner that permits flow of some food and stomach secretions around the liner 32c as indicated by arrows in FIG. 8, or it may be secured tightly against the stomach walls such that all food and stomach secretions are directed through the liner 32c. The embodiment of FIG. 8 may be provided with a distal tube similar to the tube 38 of FIG. 6.

Materials that may be used for the liners of FIGS. 5-8 include flexible materials that will prevent passage of food through the sides of the pouch. The materials may be fluid impermeable or slightly permeable. Slightly permeable materials (e.g. ePTFE with open-cell structure on the order of 20-100 micron node to fibril length) may be desirable in that they allow gastric secretions to pass into the liner without allowing food to exit.

Examples of materials useful for the liner include, but are not limited to polyesters (e.g. Dacron® polyester), ePTFE fabric (e.g. GoreTex® fabric or others), a polyurethane such as ChronoFlex® polyurethane, nylon fabrics, silicone, other polymeric materials, and bio-absorbable materials (e.g. PLLA, PGA, PCL, poly-amhydride etc). The liners may be formed of a composite of compliant, semi-compliant and/or non-compliant materials which give different regions of the sleeve/pouch different degrees of compliance so as to allow/limit expansion of the sleeve/pouch in various locations. For example, it may be desirable to provide the liner with a fairly elastic exit port to as to prevent occlusion in the event a large piece of food is ingested. The material may be coated with a lubricious, bio-compatible, chemically inert material, such as paraleyne, to reduce friction on the base.

The exterior of the liner material may be impregnated with substances known to inhibit release of Ghrelin or other hormones associated with feelings of satiety. Such substances may be chemical or pharmaceutical substances, therapeutic molecules or cells, or genetic material. The liner may also be impregnated with an acid to inhibit production of Gastrin, or its exterior may be impregnated with an anti-Gastrin antibody, or any of a variety of therapeutic drugs or molecules.

The liner may be reinforced with, constructed of, or supported by a supporting structure, such as a soft mesh, coil, a cage structure, ribs, rings etc. The supporting structure may be formed of stainless steel, polymer, shape memory materials (such as nitinol, shape memory alloys, or shape memory polymers), bio-absorbable materials or, in the case of a silicone liner, thickened regions of silicone. The supporting structure may be located at the interior or exterior of the liner material. It may be molded into or sewn to the liner material, or it may be attached using a suitable adhesive. If a tightly woven mesh or tightly wound coil is provided, the flexible material may be eliminated. Alternatively, a mesh may be provided having a polymeric material embedded in the interstices of the mesh, in which case a separate internal or external covering of liner material may be eliminated. The polymer may be impregnated with an agent that will decrease Ghrelin secretion or neutralize stomach acidity.

The inner diameter of the liner (and/or supporting structure) may be coated with lubricious material such as Teflon or parylene to ease the passage of food through the liner.

The liner is preferably constructed so as to be self-expanding, such that the pouch springs radially open into an expanded condition upon ejection from a deployment device or catheter. In one example of a method of deploying a liner such as the liners of FIGS. 5-8, the liner may be compressed and inserted into a deployment tube. In this example, the distal end of the deployment tube is inserted (preferably through the esophagus) into the stomach and the liner ejected from the tube using a pushrod passed through tube. The liner expands within the stomach, and the physician secures the liner to the stomach using sutures, clips, adhesives, stents or stent-like structures, radial forces, etc.

Figure 9:
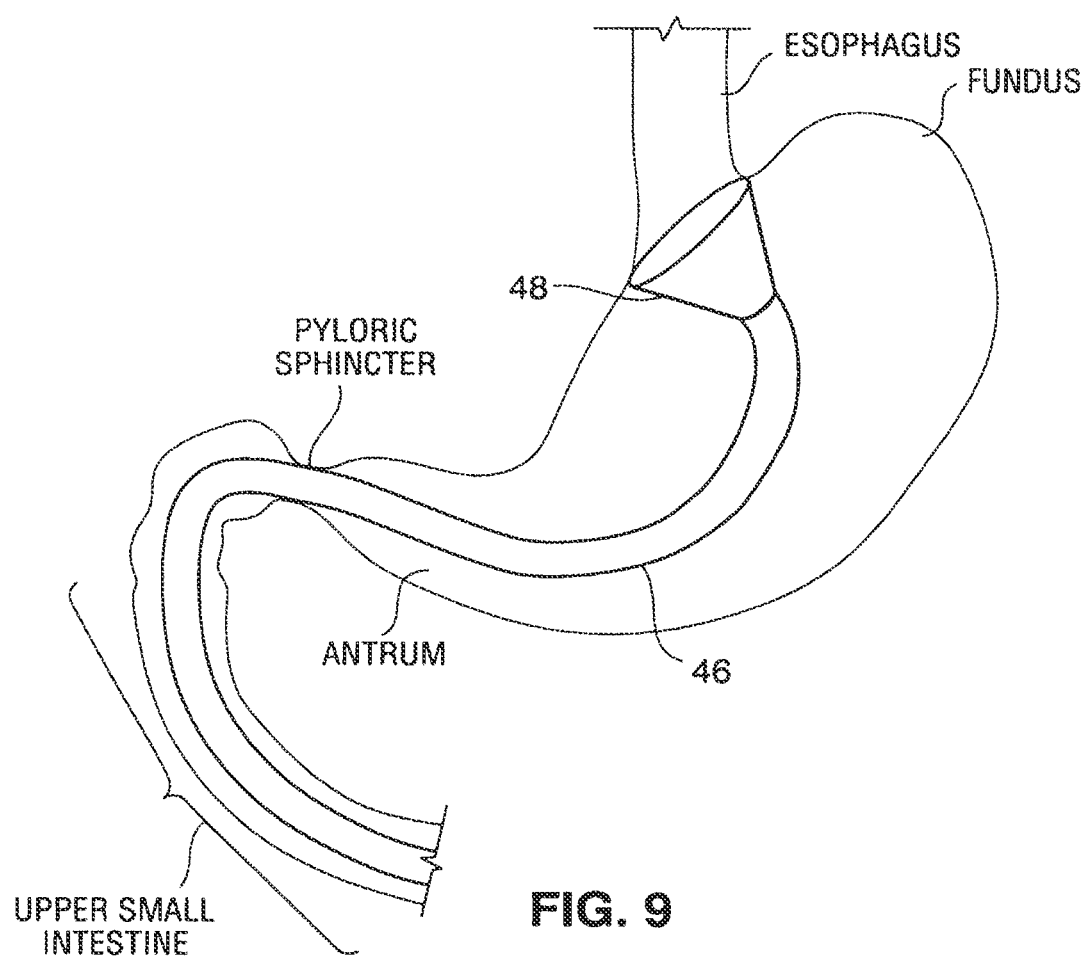
FIG. 9 is a schematic illustration of a human stomach and proximal small intestine showing positioning of a bypass tube extending from the proximal stomach into the small intestine.

FIG. 9 illustrates an alternate satiation device that includes an elongate bypass tube 46 that is implanted to extend from the proximal stomach, through the pylorus and into the small intestine (for example, through the first 24 inches of the small intestine). As with prior embodiment, tube 46 reduces the amount of contact between ingested food and the stomach and thus may eventually result in decreased Ghrelin production. It also functions similar to a Roux-en-y bypass in that it reduces the amount of surface of the small intestine that is available for absorbing food. The tube is preferably made of a thin-walled polymer that is flexible enough to allow peristalsis within the small intestine. It also bypasses the bile and pancreatic ducts, which insert digestive enzymes into the small intestine.

Figure 11:
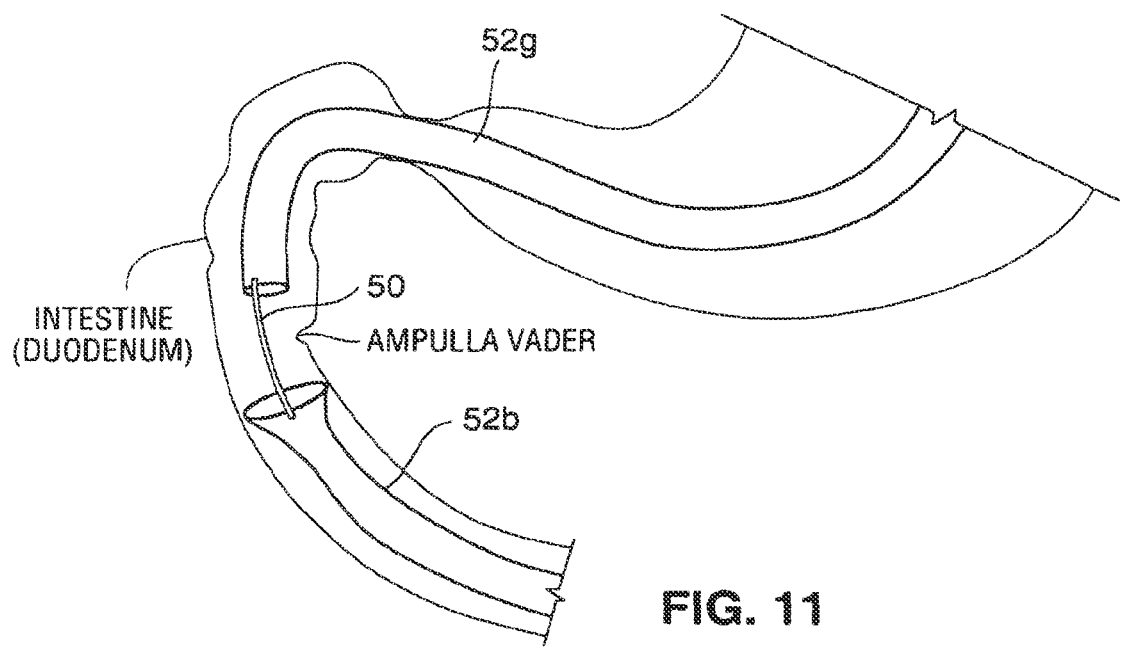
FIG. 11 is a schematic illustration of a pylorus showing a tether connecting proximal and distal portions of the tube of FIG. 9 and extending past the ampulla vader.

It may be desirable to position the tube so that it does not contact the ampulla of vader (an opening in the duodenum through which bile passes into the duodenum) so as to minimize the chance of irritation and choleocystitus. For example, a narrow tether 50 (FIG. 11) may connect the proximal portion 52a of the tube (which is disposed proximal of the ampulla vader) to the distal portion 52b of the tube so as to avoid obstructing the ampulla. Distal portion 52b may include a funnel-shaped proximal end to facilitate re-entry of food into the tube 46 after the food has passed the ampulla vader.

Lastly, referring again to FIG. 9, tube 46 may be provided with a proximal pouch 48, similar to the pouch of FIG. 3, that may distend when filled with ingested food, imparting pressure against the upper stomach and lower esophageal sphincter causing the patient to experience sensations of fullness. The pouch 48 and tube 46 may be separately implantable and then attached to one another in situ.

Figure 10A:
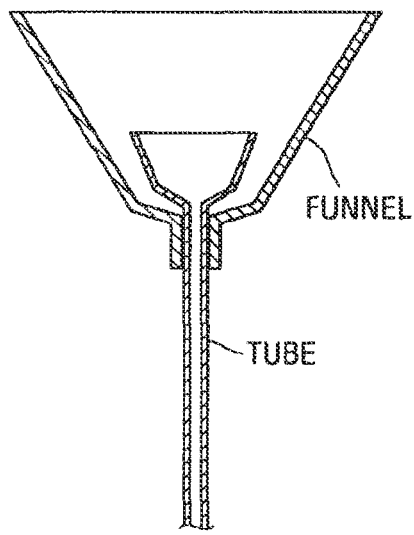
FIG. 10A is a cross-sectional side elevation view showing one example of a mechanism for attaching the pouch and the tube of FIG. 9.
Figure 10B:
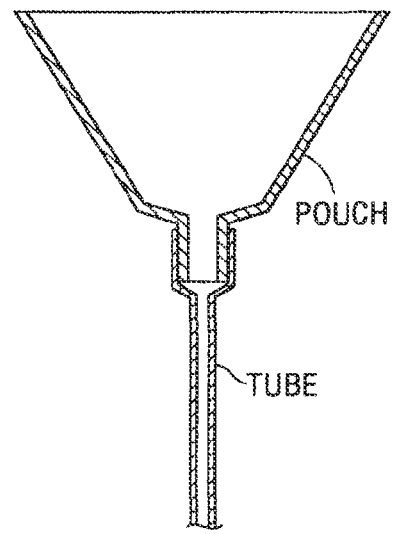
FIG. 10B is a cross-sectional side elevation view showing a second example of a mechanism for attaching the pouch and the tube of FIG. 9.

FIGS. 10A and 10B show two examples of configurations for attaching the pouch 48 and tube 46. In one configuration, the proximal end of the tube 48 may be inserted into the distal opening of the pouch 46 as shown in FIG. 10A. In another, the distal end of the pouch 46 may be inserted into the proximal end of the tube 48 as shown in FIG. 10B. Naturally, other means of attachment may be used, including sutures, hooks, stents or stent-like structures and/or adhesives.

Various embodiments of satiation devices have been described herein. These embodiments are given by way of example and are not intended to limit the scope of the present invention. It should be appreciated, moreover, that the various features of the embodiments that have been described may be combined in various ways to produce numerous additional embodiments. Moreover, while various materials, dimensions, shapes, implantation locations, etc. have been described for use with disclosed embodiments, others besides those disclosed may be utilized without exceeding the scope of the invention.

Figure 12:
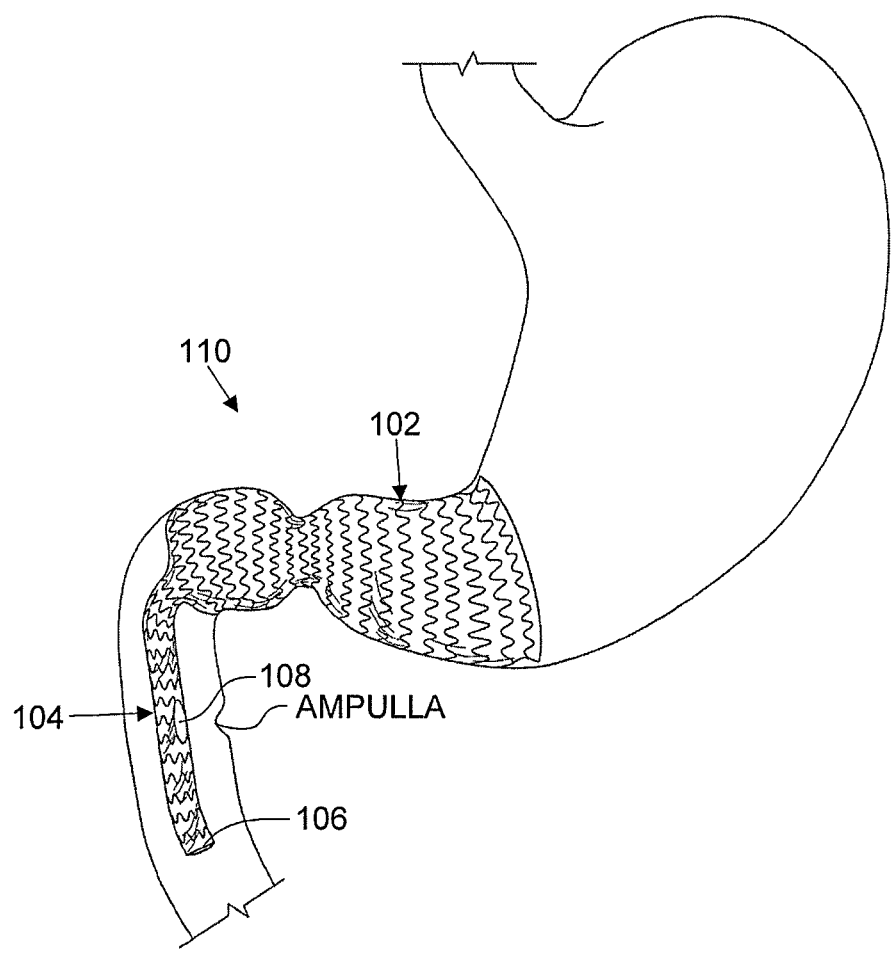
FIG. 12 is a schematic illustration showing the position of an alternative device having an antral tube and a bowel tube.

Referring to FIG. 12, an alternate embodiment of satiation device 110 includes an antral tube 102 similar to that of the previous embodiments, but additionally includes a small diameter bowel tube 104 at its distal end. The bowel tube 104 is preferably formed of a combination of mesh and polymer. It simulates a Roux en Y, or gastric bypass, procedure by keeping food away from the proximal portion of the small bowel (i.e. away from the duodenum or the jejunum and duodenum, the portions of the small intestine at which most carbohydrates and proteins are absorbed by the body). This in turn prevents absorption of food by the proximal portion of the small bowel, and thus reduces the total amount of food absorbed by the body.

The bowel tube 104 is smaller in diameter than the antral tube 102, and is of a diameter that will allow it to press gently against the walls of the small bowel. It must also be sufficiently flexible to pass posteriorly and distally into the second portion of the duodenum without damaging the mucosa. This may be facilitated by the use of a guidewire that is first introduced with an endoscope.

The bowel tube 104 may be a soft wire mesh (formed, for example, of shape memory alloys, nitinol, stainless steel alloys, stainless steel or polymers including shape memory polymers) covered with a polymer to prevent food and digestive juices from contacting the mucosa of the duodenum. Tube 104 may be provided to have a valve 106 at its distal end, which functions to prevent reflux of intestinal contents. The bowel tube includes an opening 108 to ensure that the ampulla of vader is not obstructed.

Figure 13:
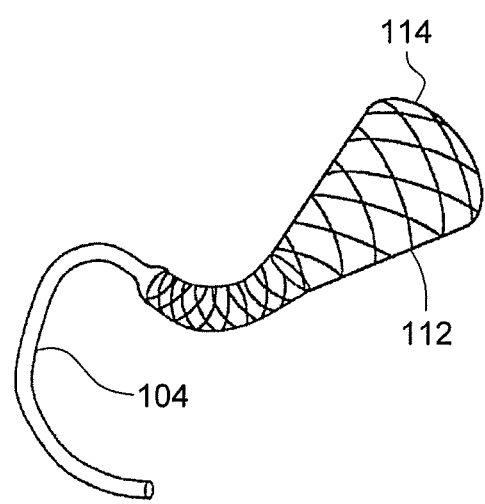
FIG. 13 is a plan view of a satiation device having an antral tube, fundal basket, and bowel tube.

Referring to FIG. 13, embodiments having an antral tube 112 and a fundal basket 114 may further include a bowel tube 104 attached to the antral tube. As discussed previously with respect to FIG. 12, the bowel tube 104 functions to keep food away from the proximal small bowel. The bowel tube 104 may have properties similar to those described with respect to the embodiment of FIG. 12.

Finally, an enclosed bypass tail (not shown) may extend from a distal opening of the pouch through the pylorus into the small bowel to simulate a stomach bypass procedure. The structure of the tail may be similar to the bowel tube described with respect to FIG. 12.

Figure 14:
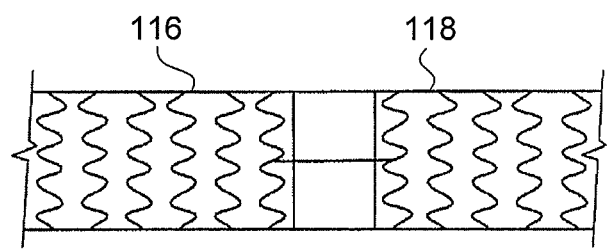
FIG. 14 is a partial side elevation view of a satiation device having an antral tube and a bowel tube. The figure illustrates a portion of the antral tube and a portion of the bowel tube.

The bowel section 116 and antral section 118 may be connected with one or more longitudinal struts, as shown in FIG. 14. An alternative embodiment may be provided without an attachment strut, in which case bowel tube 116 may be placed separately from antral tube 118, and it may include a neck section (or tabs) at its proximal edge to allow recovery with an endoscopically controlled snare. As discussed previously, a device of this type may be provided as a modular or unitary device.

We claim:

1. Apparatus for inducing weight loss in a patient having a stomach, an antrum within the stomach, a small intestines, and a pylorus connecting the antrum to the small intestine, comprising:
    a prosthesis having
    (i) a funnel shaped satiation device with proximal and distal openings, with a plurality of eyelets arranged about said proximal opening, and
    (ii) an elongate bypass tube having a proximal end joined to the distal opening of the satiation device, a first section dimensioned to extend from the proximal stomach to the pylorus, and a second section dimensioned to extend through the pylorus and into the small intestine, when the satiation device is secured to the stomach wall below the Z-line of the gastro-esophageal junction region of the patient's stomach, and being formed of a thin-walled polymer that is flexible enough to allow peristalsis within the small intestine, and
    sutures or clips for engaging said eyelets to secure the proximal opening of the satiation device of the prosthesis to the stomach wall below the Z-line of the gastro-esophageal junction region such that the proximal opening of the prosthesis receives food directly from the esophagus.

2. The apparatus of claim 1, wherein the second section of the elongate bypass tube contains a proximal portion connected to a distal portion, such that a gap between the proximal and distal portions is positioned to avoid obstruction of the ampulla of vader.

* * * * *